United States Patent
Heck et al.

(10) Patent No.: US 7,064,223 B2
(45) Date of Patent: Jun. 20, 2006

(54) METHOD FOR PRODUCING TECHNICAL OLEIC ACID METHYL ESTERS

(75) Inventors: Stephan Heck, Pulheim (DE); Volker Winterhoff, Ratingen (DE); Bernhard Gutsche, Hilden (DE); Georg Fieg, Mettmann (DE); Uwe Mueller, Monheim (DE); Jean Rigal, Tournefeuille (FR); Thomas Kapala, Ratingen (DE)

(73) Assignee: Cognis France S.A., Boussens (FR)

( * ) Notice: Subject to any disclaimer, the term of this patent is extended or adjusted under 35 U.S.C. 154(b) by 0 days.

(21) Appl. No.: 10/496,989

(22) PCT Filed: Nov. 21, 2002

(86) PCT No.: PCT/EP02/13051

§ 371 (c)(1),
(2), (4) Date: Dec. 17, 2004

(87) PCT Pub. No.: WO03/045891

PCT Pub. Date: Jun. 5, 2003

(65) Prior Publication Data

US 2005/0090676 A1   Apr. 28, 2005

(30) Foreign Application Priority Data

Nov. 30, 2001 (FR) .................................. 01 15503

(51) Int. Cl.
*C07C 51/43* (2006.01)
(52) U.S. Cl. ....................... 554/175; 514/724; 514/739; 568/881; 568/884; 554/224

(58) Field of Classification Search ................ 554/224, 554/175; 514/739, 724; 568/881, 884

See application file for complete search history.

(56) References Cited

U.S. PATENT DOCUMENTS

2002/0035159 A1* 3/2002 Heck et al. .................. 514/739
2002/0037932 A1* 3/2002 Heck et al. .................. 514/724

FOREIGN PATENT DOCUMENTS

| DE | 41 24 517 | 1/1993 |
| EP | 0 460 917 | 12/1991 |
| EP | 0 610 506 | 8/1994 |
| WO | WO 98/42646 | 10/1998 |
| WO | WO 99/25674 | 5/1999 |

OTHER PUBLICATIONS

H. Schmid, "Möglichkeiten der Fettchemie für die Schmlermittelindustrie", Fett Wissenschaft Technologie—Fat Science Technology, vol. 89, No. 6, 1987, pp. 237-248'; XP002232102.

* cited by examiner

*Primary Examiner*—Deborah D. Carr
(74) *Attorney, Agent, or Firm*—John F. Daniels

(57) ABSTRACT

A process for making technical oleic acid methyl esters having a stearic acid methyl ester content of less than about 2% by weight, and a palmitic acid methyl ester content of less than about 5%, comprising: (a) providing a $C_{8-18}$ palm kernel oil fatty acid methyl ester; (b) fractionally distilling said $C_{8-18}$ palm kernel oil fatty acid methyl ester to form a $C_{8-14}$ head product and a $C_{16-18}$ bottom product; (c) fractionally distilling the $C_{16-18}$ bottom product to form a short-chain $C_{16}$ head product and a long-chain and unsaturated $C_{18}$ bottom product; (d) fractionally distilling the long-chain and unsaturated $C_{18}$ bottom product to form a predominantly unsaturated head product having a high palmitic acid methyl ester content and a predominantly unsaturated bottom product have a minimal palmitic acid methyl ester content; and (e) fractionally distilling the predominantly unsaturated bottom product have a minimal palmitic acid methyl ester content to form a head product rich in oleic acid methyl ester and poor in stearic acid methyl ester and a bottom product rich in both oleic acid methyl ester and stearic acid methyl ester.

11 Claims, No Drawings

METHOD FOR PRODUCING TECHNICAL OLEIC ACID METHYL ESTERS

BACKGROUND OF THE INVENTION

This application is a 371 of PCT/EP02/13051 filed Nov. 21, 2002.

This invention relates generally to the field of oleochemistry and, more particularly, to a process for the production of technical oleic acid methyl esters with a low stearic acid methyl ester content by multiple fractionation of palm kernel oil fatty acid methyl ester.

Unsaturated fatty alcohols with iodine values in the range from 80 to 100 are valuable raw materials for the production of detergents and cosmetics. These compounds are synthesized by reduction of the corresponding technical oleic acid methyl esters which, because of their natural origin, always contain saturated homologs. However, in order to guarantee satisfactory low-temperature behavior, the content of stearic acid methyl ester in these starting materials has to be below 2% by weight. To guarantee this, the fatty acids on which the esters are based are normally subjected to separation of wetting agent ("rolling-up") or to solvent crystallization (Emersol process) which, on the one hand, is expensive on equipment and, on the other hand, makes the simpler method of producing the esters by transesterification of the triglycerides impossible. Alternatively, fractional crystallization could also be carried out at the alcohol stage (WO 98/42646, Cognis) although this would also involve an additional processing step and is therefore undesirable.

Accordingly, the problem addressed by the present invention was to find an alternative process for the production of oleic acid methyl esters with methyl stearate contents of or below 2% by weight which would not be attended by any of the disadvantages mentioned above. In particular, the process would not require additional crystallization steps and could be operated continuously. Preferably, the process would provide oleic acid methyl esters in a purity of at least 75% by weight.

DESCRIPTION OF THE INVENTION

The present invention relates to a process for the production of technical oleic acid methyl esters with stearic acid methyl ester contents of or below 2% by weight and palmitic acid methyl ester contents of or below 5% by weight. The starting mixture is palm kernel oil fatty acid methyl ester (PKFAME C8–18) which is first subjected to fractional distillation so that PKFAME C8–14 accumulates in the head product and PKFAME C16–18 accumulates in the bottom product. Now, the present invention relates to a process for further processing the bottom fraction (PKFAME C16–18) which is characterized in that (a) PKFAME C16–18 is subjected to a first fractional distillation to form a relatively short-chain head product (PKFAME C16) and a predominantly relatively long-chain and unsaturated bottom product (PKFAME C18) and (b) the first bottom product thus obtained is subjected to a second fractional distillation to form a predominantly unsaturated head product with a high palmitic acid methyl ester content and a likewise predominantly unsaturated bottom product with a minimal palmitic acid methyl ester content and (c) the second bottom product thus obtained is subjected to a third fractional distillation to form a head product rich in oleic acid methyl ester and poor in stearic acid methyl ester and a bottom product rich in oleic acid methyl ester and stearic acid methyl ester.

The end product is a mixture of the head products from stages two and three.

It has surprisingly been found that the defined separation of palm kernel oil fatty acid methyl ester ultimately leads to an oleic acid methyl ester which has a purity of at least 75% by weight, is substantially free from stearic acid methyl ester and has a palmitic acid methyl ester content of less than 5% by weight without rolling-up or fractional crystallization having to be included to achieve this result. The number of process steps does not necessarily have to be three, as described above, but is governed by the technical requirements of the distillation unit. However, there should be at least two separation steps. The first step comprises the separation of the PKFAME C16 while the second step involves the separation of the unsaturated PKFAME C18 from the saturated PKFAME C18. The second separation step is the more elaborate and presupposes a very large number of theoretical separation stages so that, for reasons of pressure loss and the particular evaporation principle at the bottom of the distillation unit, the second separation step may have to be divided up between several columns each with a relatively small number of theoretical separation stages. The number of process steps would therefore be greater than two.

First Fractionation—Separation of PKFAME C16

All three fractionation steps may be carried out in known manner. The main object of the first stage of the process is to remove most of the unwanted palmitic fatty acid methyl ester. To this end, the feed is heated to the boiling temperature and is fed in between the sublimating section and the stripping section of a fractionating column. The column is preferably provided with a packing, for example a Sulzer Melapak. The first fractionation is preferably carried out at a temperature of 160 to 200° C. and, more particularly, at a temperature of 180 to 190° C. and under a reduced pressure of 10 to 25 mbar, the pressure drop in the column normally amounting to about 15 mbar. The reflux ratio may be 2 to 3:1. A first head product containing at least 90 and preferably 95 to 99% by weight of palmitic acid methyl ester is prepared in this way. At the same time, a first bottom product containing at least 70 and preferably 70 to 75% by weight of oleic acid methyl ester is obtained. The process parameters, such as the reflux ratio for example, may vary because they are dependent on the composition of the feed.

Second Fractionation

The main object of the second stage of the process is to remove the remaining palmitic acid methyl ester and to concentrate already unsaturated PKFAME C18 in the head product. The second fractionation is preferably carried out at a temperature of 200 to 230° C. and more particularly at a temperature of 210 to 220° C. and under a reduced pressure of 10 to 25 mbar, the pressure drop in the column normally amounting to about 15 mbar. The reflux ratio may be 8 to 12:1. A second head product still containing at least 1 and preferably 10 to 15% by weight palmitic acid methyl ester and at least 60% by weight and preferably 65 to 80% by weight oleic acid methyl ester is prepared in this way. At the same time, a second bottom product containing at most 1% by weight palmitic acid methyl ester and at least 70 and preferably 70 to 75% by weight oleic acid methyl ester is obtained.

Third Fractionation

The object of the third and final step of the process is substantially quantitatively to remove the stearic acid methyl ester, i.e. to leave it in the bottom of the column. The third fractionation is preferably carried out at a temperature of 200 to 230° C. and more particularly at a temperature of 210 to 220° C. and under a reduced pressure of 10 to 25 mbar, the pressure drop in the column normally amounting to about 15 mbar. The reflux ratio may be 5 to 10:1. A third head product containing at least 75 and preferably 80 to 85% by weight oleic acid methyl ester and less than 2% by weight stearic acid methyl ester is prepared in this way. The two head products from stages 2 and 3 represent the target product. The head product from stage 1 and the bottom product from stage 3 may either be returned to the circuit to increase the yield or may be used for other purposes.

EXAMPLES

Example 1

Palm kernel oil fatty acid methyl ester fraction (PKFAME C16–18) was heated to 180° C. at a throughput of 2,000 kg/h a continuously fed in between the sublimating and stripping sections of a first packed fractionating column. With a head vacuum of 10 mbar, a bottom vacuum of 25 mbar and a reflux ratio of 2:1, 502 kg/h of a head product H1 and 1498 kg/h of a bottom product B1 (boiling point 219.2° C.) were obtained. The bottom product was fed into a second packed fractionating column between the sublimating and stripping sections at a throughput of 1498 kg/h and at a temperature of 219.2° C. With a head vacuum of 10 mbar, a bottom vacuum of 25 mbar and a reflux ratio of 10:1, 150 kg/h of a head product H2 and 1348 kg/h of a bottom product B2 (boiling point 219.7° C.) were obtained. The bottom product was fed into a third packed fractionating column between the sublimating and stripping sections at a throughput of 1348 kg/h and at a temperature of 219.7° C. With a head vacuum of 10 mbar, a bottom vacuum of 25 mbar and a reflux ratio of 5.5:1, 582 kg/h of a head product H3 and 766 kg/h of a bottom product B3 (boiling point 229.5° C.) were obtained. The yield, defined as the quotient of the end product (unsaturated methyl ester) and the feed (starting material), was 53.1%. The compositions of the products are shown in Table 1.

TABLE 1

Composition of the methyl ester fractions (figures = % by weight)

|  | PKFAME | H1 | B1 | H2 | B2 | H3 | B3 |
|---|---|---|---|---|---|---|---|
| C16:0 ME | 25.12 | 96.16 | 1.32 | 13.03 | 0.01 | 0.03 | 0 |
| C18:2 ME | 10.08 | 0.87 | 13.17 | 18.24 | 12.60 | 18.28 | 8.29 |
| C18:1 ME | 55.73 | 2.91 | 73.43 | 66.84 | 74.17 | 80.12 | 69.64 |
| C18:0 ME | 9.07 | 0.07 | 12.09 | 1.89 | 13.22 | 1.57 | 22.07 |

Example 2

Palm kernel oil fatty acid methyl ester fraction (PKFAME C16–18) was heated to 180° C. at a throughput of 830 kg/h and fed in between the sublimating and stripping sections of a first packed fractionating column. With a head vacuum of 10 mbar, a bottom vacuum of 25 mbar and a reflux ratio of 2.5:1, 208 kg/h of a head product H1 and 622 kg/h of a bottom product B1 (boiling point 219.5° C.) were obtained. The bottom product was fed into a second packed fractionating column between the sublimating and stripping sections at a throughput of 622 kg/h and at a temperature of 219.5° C. With a head vacuum of 10 mbar, a bottom vacuum of 25 mbar and a reflux ratio of 10:1, 152 kg/h of a head product H2 and 470 kg/h of a bottom product B2 (boiling point 219.8° C.) were obtained. The bottom product was fed into a third packed fractionating column between the sublimating and stripping sections at a throughput of 470 kg/h and at a temperature of 219.8° C. With a head vacuum of 10 mbar, a bottom vacuum of 25 mbar and a reflux ratio of 9:1, 365 kg/h of a head product H3 and 105 kg/h of a bottom product B3 (boiling point 231.4° C.) were obtained. The yield, defined as the quotient of the end product (unsaturated methyl ester) and the feed (starting material), was 92.8%. The compositions of the products are shown in Table 2.

TABLE 2

Composition of the methyl ester fractions (figures = % by weight)

|  | PKFAME | H1 | B1 | H2 | B2 | H3 | B3 |
|---|---|---|---|---|---|---|---|
| C16:0 ME | 25.12 | 99.32 | 0.31 | 1.26 | 0 | 0 | 0 |
| C18:2 ME | 10.08 | 0.16 | 13.40 | 20.67 | 11.04 | 13.69 | 1.84 |
| C18:1 ME | 55.73 | 0.51 | 74.20 | 76.13 | 73.57 | 64.43 | 34/44 |
| C18:0 ME | 9.07 | 0.01 | 12.10 | 1.94 | 15.39 | 1.48 | 63.72 |

The invention claimed is:

1. A process for making technical oleic acid methyl esters having a stearic acid methyl ester content of less than about 2% by weight, and a palmitic acid methyl ester content of less than about 5%, comprising:
   (a) providing a $C_{8-18}$ palm kernel oil fatty acid methyl ester;
   (b) fractionally distilling said $C_{8-18}$ palm kernel oil fatty acid methyl ester to form a $C_{8-14}$ head product and a $C_{16-18}$ bottom product;
   (c) fractionally distilling the $C_{16-18}$ bottom product to form a short-chain $C_{16}$ head product and a long-chain and unsaturated $C_{18}$ bottom product;
   (d) fractionally distilling the long-chain and unsaturated $C_{18}$ bottom product to form a predominantly unsaturated head product having a high palmitic acid methyl ester content and a predominantly unsaturated bottom product have a minimal palmitic acid methyl ester content; and
   (e) fractionally distilling the predominantly unsaturated bottom product have a minimal palmitic acid methyl ester content to form a head product rich in oleic acid methyl ester and poor in stearic acid methyl ester and a bottom product rich in both oleic acid methyl ester and stearic acid methyl ester.

2. The process of claim 1 wherein (c) is performed at a temperature of from about 160 to 200° C. and under a pressure of from about 10 to 25 mbar.

3. The process of claim 1 wherein the short-chain $C_{16}$ head product has a palmitic acid methyl ester content of at least 90% by weight.

4. The process of claim 1 wherein the long-chain $C_{18}$ bottom product has an oleic acid methyl ester content of at least 70% by weight.

5. The process of claim 1 wherein (d) is performed at a temperature of from about 200 to 230° C. and under a pressure of from about 10 to 25 mbar.

6. The process of claim 1 wherein the predominantly unsaturated head product of step (d) contains at least 1% by weight of palmitic acid methyl ester and at least 50% by weight of oleic acid methyl ester.

7. The process of claim 1 wherein the predominantly unsaturated bottom product of step (d) contains at most 1% by weight of palmitic acid methyl ester and at least 70% by weight of oleic acid methyl ester.

8. The process of claim 1 wherein (e) is performed at a temperature of from about 210 to 230° C. and under a pressure of from about 10 to 25 mbar.

9. The process of claim 1 wherein the head product of step (e) contains at least 75% by weight of oleic acid methyl ester and less than 2% by weight of stearic acid methyl ester.

10. The process of claim 1 wherein the bottom product of step (e) contains at most 30% by weight of oleic acid methyl ester and at least 20% by weight of stearic acid methyl ester.

11. The process of claim 1 further comprising mixing the predominantly unsaturated head product of step (d), with the head product of step (e) to form a final product having at least 75% by weight of oleic acid methyl ester, at most 5% by weight of palmitic acid methyl ester, and up to 2% by weight of stearic acid methyl ester.

* * * * *